US011350827B2

(12) United States Patent
Marra et al.

(10) Patent No.: US 11,350,827 B2
(45) Date of Patent: Jun. 7, 2022

(54) PORTABLE DEVICE FOR THE ANALYSIS OF SKIN TRAUMAS AND METHOD FOR ANALYZING SKIN TRAUMAS USING A PORTABLE DEVICE

(71) Applicants: Sociedade Beneficente Israelita Brasileira Hospital Albert Einstein, São Paulo (BR); I-HealthSys Produtos Médicos Ltda—ME, São Carlos (BR)

(72) Inventors: Alexandre Rodrigues Marra, Sao Paulo (BR); Oscar Fernando Pavao Dos Santos, Sao Paulo (BR); Marcelo Prado, Sao Carlos (BR); Renaldo Massini Junior, Sao Carlos (BR); Guilherme Machado Gagliardi, Sao Carlos (BR); Felipe Kermentz Ferraz Costa, Sao Carlos (BR); Tales Roberto De Souza Santini, Muzambinho (BR); Alvaro Costa Neto, Sao Carlos (BR)

(73) Assignees: Sociedade Beneficente Israelita Brasileira Hospital Albert Einstein, São Paulo (BR); I-HealthSys Produtos Médicos Ltda—ME, São Carlos (BR)

(*) Notice: Subject to any disclaimer, the term of this patent is extended or adjusted under 35 U.S.C. 154(b) by 304 days.

(21) Appl. No.: 15/440,872

(22) Filed: Feb. 23, 2017

(65) Prior Publication Data
US 2018/0042487 A1 Feb. 15, 2018

(30) Foreign Application Priority Data
Aug. 15, 2016 (BR) .................... BR102016018763-0

(51) Int. Cl.
*A61B 5/01* (2006.01)
*A61B 5/00* (2006.01)

(52) U.S. Cl.
CPC ............ *A61B 5/015* (2013.01); *A61B 5/0059* (2013.01); *A61B 5/445* (2013.01); *A61B 5/743* (2013.01); *A61B 2560/0431* (2013.01)

(58) Field of Classification Search
CPC .......... A61B 2560/0431; A61B 5/0059; A61B 5/015; A61B 5/445; A61B 5/743
See application file for complete search history.

(56) References Cited

U.S. PATENT DOCUMENTS

| 6,993,167 B1 * | 1/2006 | Skladnev ................. G06K 9/00 382/128 |
| 2008/0146912 A1 * | 6/2008 | Richard ................. A61B 5/015 600/411 |

(Continued)

*Primary Examiner* — Yi-Shan Yang
*Assistant Examiner* — Alexei Bykhovski
(74) *Attorney, Agent, or Firm* — Patterson + Sheridan, LLP

(57) ABSTRACT

A portable device for the analysis of skin traumas is disclosed, the device allowing the medical professional to evaluate and analyze the healing process of the skin traumas, providing the medical professional with the temperature parameters, distance parameters and diagnosis parameters related to the skin trauma. By using the proposed portable device, it is possible, for example, to evaluate if the dimensions of the skin trauma have changed throughout the time, and also to generate a temperature map of the skin trauma as well as a history of conducted analyses. The present invention further discloses a method for analyzing skin traumas by using a portable device.

14 Claims, 5 Drawing Sheets

(56) References Cited

U.S. PATENT DOCUMENTS

| | | | |
|---|---|---|---|
| 2009/0318908 A1* | 12/2009 | Van Pieterson | A61B 5/0059 606/9 |
| 2011/0054310 A1* | 3/2011 | Taylor | A61B 5/0059 600/425 |
| 2011/0118608 A1* | 5/2011 | Lindner | A61B 5/015 600/474 |
| 2011/0215930 A1* | 9/2011 | Lee | G06K 9/00 340/573.1 |
| 2013/0162796 A1* | 6/2013 | Bharara | A61B 5/0077 348/77 |
| 2015/0265159 A1* | 9/2015 | Lane | A61B 5/01 600/549 |
| 2018/0014734 A1* | 1/2018 | Rogers | A61B 5/0048 |

* cited by examiner

PORTABLE DEVICE FOR THE ANALYSIS OF SKIN TRAUMAS AND METHOD FOR ANALYZING SKIN TRAUMAS USING A PORTABLE DEVICE

The present invention relates to a portable device for the analysis of skin traumas (wounds). More specifically, the present invention relates to a portable device capable of checking the healing process of a skin trauma. It also discloses a method for analyzing skin traumas using a portable device.

DESCRIPTION OF THE PRIOR ART

The analysis of skin traumas (bruises, wounds, lesions), and more specifically, the analysis of the healing process of a skin trauma is usually made by a medical professional that periodically views the lesion exposed in the skin of a patient.

The medical professional is responsible for viewing and evaluating the wound, for example, according to the size of the injured area, if the healing process is progressing or not.

In other words, the medical professional evaluates, by viewing the wound, if its size decreased or increased and then reveals the diagnosis to the patient.

For more severe (acute) skin traumas, some equipment may assist the medical professional in evaluating the treatment of the injury, however, said equipment is of a large size and in order to use it, it is necessary to schedule an appointment with the medical staff and to reserve an exclusive room at the hospital/office.

Such equipment, due to its large size, cannot be arranged in emergency are units such as ambulances or firefighting teams.

The prior art discloses a few small-sized equipment for the analysis of skin parameters, but they focus excessively on the analysis of the patient's temperature and do not provide information, for example, on the wound area, geometry, map of temperature and dimensions between outermost edges.

As an example, mention may be made of document US 2005/0169347, wherein a portable temperature sensor is disclosed. The proposed device uses infrared sensors and captures only the temperature at a given specific point, not capturing an image of the area under analysis.

Additionally, said document does not specifically describe its use for the analysis of the wound healing process, being specific only for temperature measurement at certain points.

The same occurs in the apparatus disclosed in document US 2013/0235901, which only serves for temperature measurement, but cannot be used as portable device for the analysis of the wound healing process as proposed in the present invention.

Thus, there is a gap in the prior art when it comes to the proposition of a small-sized, portable device that is able, for example, to be transported by a medical professional in its pocket or workbook and also to analyze the skin trauma healing process.

The present invention proposes a device such as that cited above and also providing a history of the analysis of skin traumas of several patients, capable of storing said analysis history and updating it according to new analysis.

In addition to the characteristics cited above, the portable device proposed in the present invention has the function of providing the medical professional with a series of diagnosis parameters related to the analysis of skin trauma.

For example, the proposed device evaluates if the dimensions of the skin trauma have changes from a measurement to the other, and consequently, which is the current size and its decrease/increase percentage when compared to a previous measurement.

Also only as an example, the portable device proposed in the present invention is capable of generating a temperature map of the skin trauma, thus showing the regions having different temperatures (wherein said regions can be predetermined by the medical professional), and also of determining the geometry of the skin trauma.

The device is further capable of storing said diagnosis parameters in its database, thereby allowing an accurate follow-up of the skin trauma healing process by the medical professional. Said follow-up cannot be made by the matter disclosed in the art.

Said device can also, if desirable by the medical staff, send the analyzed skin parameters to a remote device such as the doctor's personal computer or a treatment unit at a hospital.

Thus, a portable device having the functionalities commented above and additional characteristics and elements which are described throughout the present specification is proposed.

OBJECTIVES OF THE INVENTION

The present invention has the objective of providing a portable device for the analysis of skin traumas that is capable of providing the medical professional with an accurate follow-up of the skin trauma healing process.

An additional objective of the present invention is to provide a portable device for the analysis of skin traumas capable of detecting the temperature of the injured area as well as the distance of the skin trauma in relation to the portable device.

Further, the present invention has the objective of providing a portable device for the analysis of skin traumas capable of measuring the local temperature, mean temperature, the maximum temperature and the minimum temperature of the skin trauma.

It is also an objective of the present invention to provide a portable device for the analysis of skin traumas capable of informing the medical professional of the geometry, the area, the temperature map and the dimensions between the outermost edges of the skin trauma.

The present invention has the further objective to provide a portable device for the analysis of skin traumas capable of generating a history of the measurement analyses (analyses) performed at different periods of time.

An additional objective of the present invention is to provide a portable device for the analysis of skin traumas capable of providing the medical professional with a diagnosis parameter of the skin trauma.

Furthermore, the present invention has the objective to provide a portable device for the analysis of skin traumas capable of exporting the detected parameters of the skin trauma to a remote device.

Finally, the present invention has the objective to provide a method for analyzing skin traumas using a portable device in accordance with the proposed portable device.

BRIEF DESCRIPTION OF THE INVENTION

It is disclosed a portable device for the analysis of skin traumas, the device comprising a main body and characterized in that it is equipped with: at least one infrared element associated with the main body, wherein the infrared element is configured so as to generate at least one temperature parameter of the skin trauma. The device further comprises at least one distance sensor associated with the main body and configured so as to generate at least one distance parameter of the skin trauma in relation to the infrared element.

It is also disclosed a method for analyzing skin traumas using a portable device, the method comprising the steps of: directing the portable device to the skin trauma, generating a temperature parameter and a distance parameter of the skin trauma, the temperature parameter corresponding to at least one of the following skin trauma parameters: local temperature, mean temperature, maximum temperature and minimum temperature.

SUMMARIZED DESCRIPTION OF THE FIGURES

Below, the present invention will be thoroughly described based on an embodiment example displayed in the figures. The figures show:

FIG. 3 is a display of the screen of the portable device proposed in the present invention, wherein

DETAILED DESCRIPTION OF THE FIGURES

Figure 1:
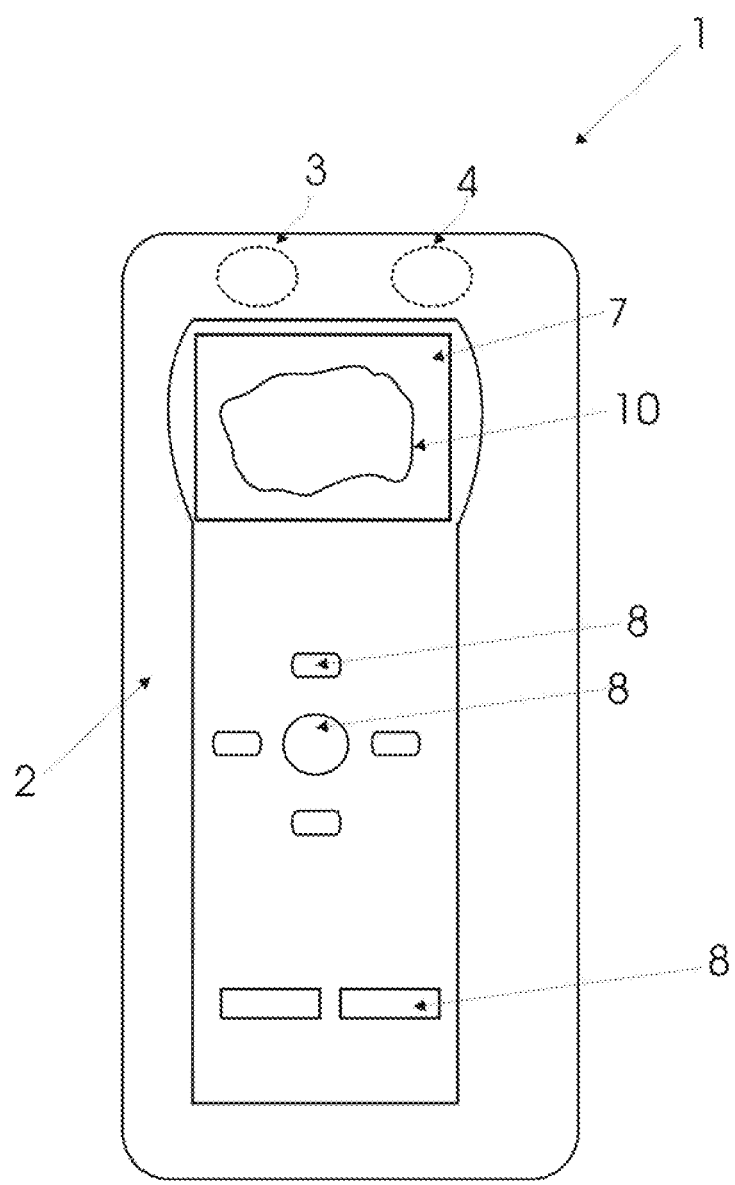
FIG. 1 is a front view of a preferred embodiment of the portable device for the analysis of skin traumas proposed in the present invention.

FIG. 1 illustrates a front view of the portable device for the analysis of skin traumas 1 proposed in the present invention, hereinafter referred to only as device 1.

By skin trauma 10 (FIG. 2) it is meant any injury (wound, bruise, cut, suture) on the skin of a patient, such as a wound caused, for example, in a traffic accident or a suture due to a postoperative period.

Figure 2:
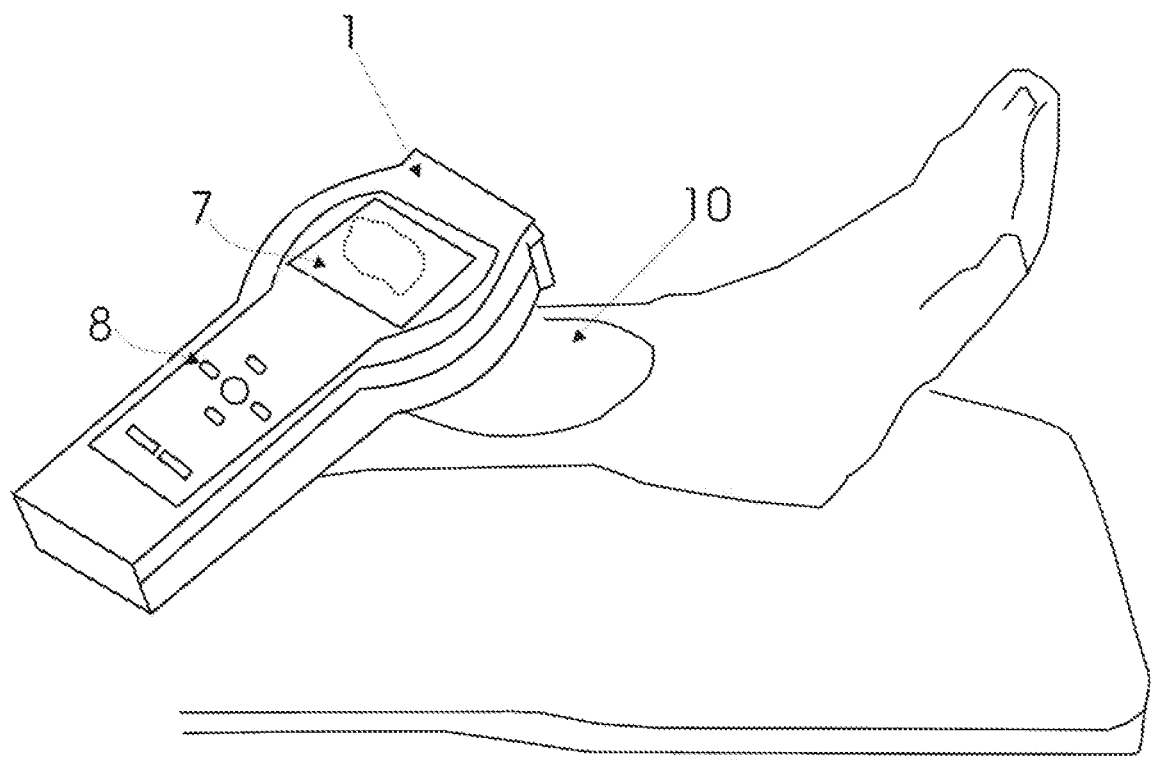
FIG. 2 is a display of the portable device for the analysis of skin traumas proposed in the present invention in use for the analysis of a wound located on the leg of a patient.

The description of this preferred embodiment of device 1 will refer to a skin trauma 10 on the leg of a patient, as shown in FIG. 2. Obviously, such a description is only preferential and should not be considered as a limitation of the present invention.

With respect to FIG. 1, it is noted that the proposed device 1 basically comprises a main body 2 preferably of rectangular shape and dimensions compatible with that of a portable apparatus.

In an alternative embodiment, the main body 2 could assume a substantially horizontal disposition, as opposed to the vertical arrangement proposed in FIG. 1.

Thus, it should be noted that the preferred shape illustrated for device 1 in FIG. 1 shall not result in any limitation of the scope of protection of the proposed device, so that other shapes would be obviously fully accepted.

From FIG. 1 it can be seen that device 1 further comprises a screen 7 for visualization of the skin trauma 10 under analysis. The dimensions and the type of screen 7 may vary according to the dimensions of device 1, however, it should be considered a suitable dimension for a satisfactory visualization of the skin trauma 10 and of the information provided by device 1.

As with the shape of device 1, the dimensions of the screen 7 exposed in FIG. 1 must be considered only as preferred.

Preferably, device 1 further comprises navigation keys 8, thus enabling navigation through all its functions. The arrangement of said navigation keys 8, as shown in FIG. 1, is only a preferred embodiment of the present device and shall not be considered as a limitation thereof.

Alternatively, the navigation between the functions of device 1 could be made on the screen 7 itself, in which case, the screen must be configured as a touch screen.

In the rear portion of the main body 2, and as preferably shown in FIG. 1 by dashed lines, device 1 comprises at least one infrared element 3, such as an infrared camera 3 and a distance sensor 4, preferably configured as a distance sensor via ultrasound or laser. It should be noted that the disposition of the infrared element 3 and of the distance sensor 4 as shown in FIG. 1, does not result in any limitation of the scope of the present invention. In alternative embodiments, these could be arranged in any portion of device 1.

In order to use device 1, the face of the main body 2 comprising the infrared element 3 (infrared camera 3) should be brought closer and directed to a skin trauma 10, as illustrated in FIG. 2.

The navigation through keys 8 allows the user of device 1 to select which parameters should be analyzed, so that the device 1 proposed in the present invention is able to generate the following parameters from the analysis of the skin trauma 10: temperature parameters 20, distance parameters 21 and image parameters 22.

With respect to the temperature parameters 20, the proposed device 1 is able to detect at least the local temperature 20', the mean temperature 20", the maximum temperature 20''' and the minimum temperature 20'''' of a skin trauma 10.

As for the distance parameter 21, device 1 is configured so as to detect the distance of the skin trauma 10 in relation to the main body 2, and more specifically the distance between the skin trauma 10 and the distance sensor 4.

Regarding the image parameter 22, device 1 is, in turn, configured so as to generate a geometry 22' of the trauma 10, determine an area 22" thereof, a temperature map 22''' and dimensions between outermost edges 22'''' of the skin trauma 10.

FIG. 3 shows a display of the screen 7 of device 1, wherein FIG. 3 (a) shows the screen 7 when the device is used for the analysis of temperature parameters 20 of the skin trauma 10 and FIG. 3 (b) shows the screen 7 when the device is used for the analysis of image parameters 22 of the skin trauma 10.

When in use for the analysis/determination of temperature parameters 20, and via infrared element 3 (infrared camera 3), the medical professional will be provided with the local temperature 20' of a specific point of the skin trauma 10 (point, to which the infrared beam is directed), the mean temperature 20" of the trauma 10, as well as its maximum 20''' and minimum temperature 20''''.

As cited above, the determination of the point of the skin trauma 10, at which the local temperature 20' will be measured can be shown to the doctor by a visible light bean directed form the infrared element 3.

In this way, the doctor can evaluate the local temperature 20' of any point of the skin trauma 10.

Additionally, besides displaying the local temperature 20' of the skin trauma 10 and its value, device 1 is also configured so as to display to the user the location of the maximum temperature and of the minimum temperature of the skin trauma.

Figure 3A:
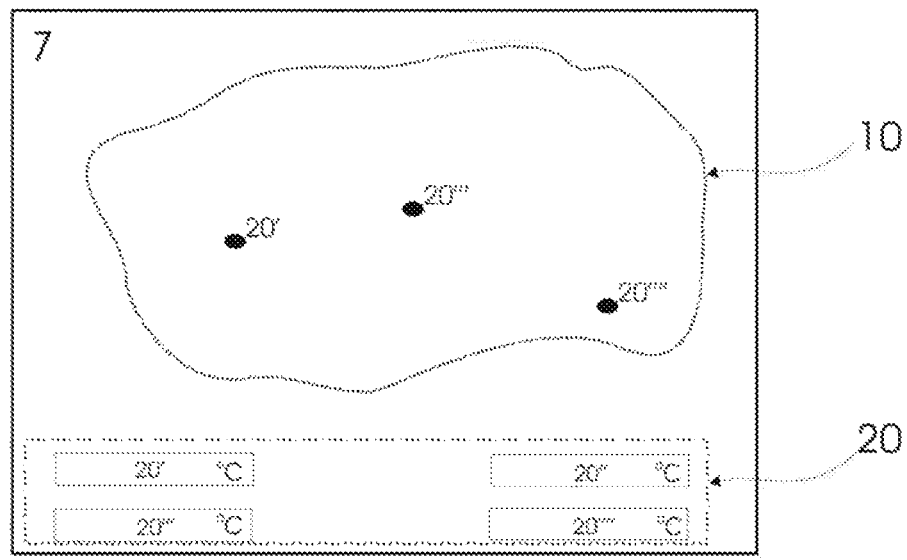
FIG. 3(a) illustrates the screen when the device is used for the analysis of temperature parameters and FIG. 3(b) illustrates the screen when the device is used for the analysis of image parameters of the skin trauma.

Said information is displayed on the screen 7, as shown in FIG. 3(a), where the points of maximum 20''' and minimum 20'''' temperatures of the skin trauma are represented.

Figure 3B:
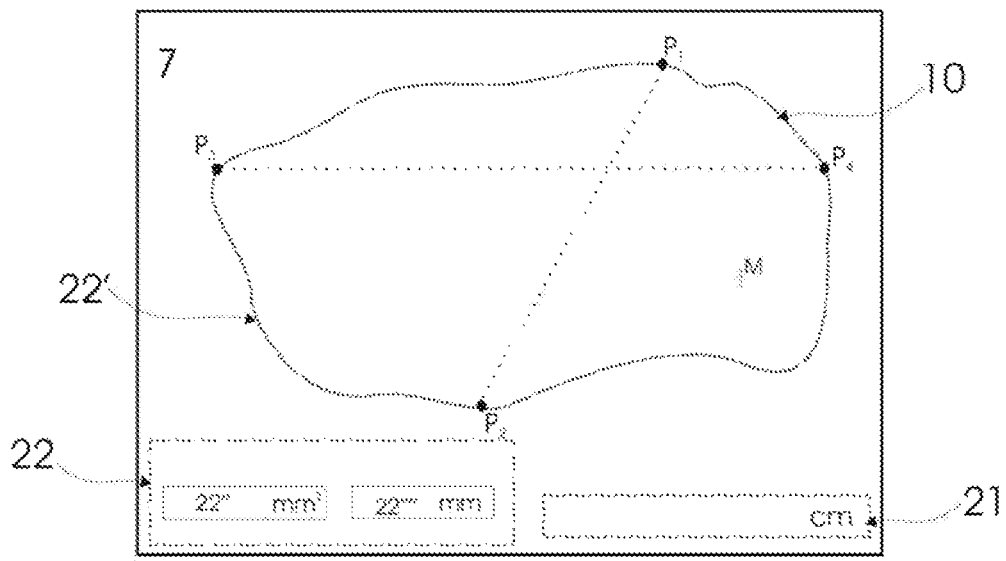

With regard to FIG. 3(b), it shows the screen 7 of device 1, when the selected function is the analysis of image parameters 22 of the skin trauma 10, and more specifically the analysis of the geometry 22', area 22'' and dimensions between outermost edges 22'''' of the skin trauma 10.

By geometry 22' of the skin trauma 10 is meant the outlines of the trauma 10, as shown in FIG. 3(b). As for the area 22'', it represents the approximate area of the skin trauma 10 established by said geometry 22''.

Preferably, device 1 is further able to determine the approximate distance between the outermost edges of the skin trauma 10, both vertically and horizontally.

In this regard, and considering FIG. 3(b) as reference, if the selected function is to determine the vertical dimensions between the outermost edges 22'''', the doctor will be provided with the dimension (distance) between points P1 and P2. Alternatively, if the selected function is to determine the horizontal dimensions between the outermost edges 22'''', the doctor will be provided with the dimension (distance) between points P3 and P4. The display of both distances (vertical and horizontal) is also valid.

A guideline between said edges, as well as the disposition thereof on the periphery of the skin trauma 10, can be displayed to the doctor on the screen 7, as shown in FIG. 3(b).

In addition to determining the dimension between the outermost edges 22'''' of the trauma, device 10 is also able to generate a distance parameter of the skin trauma 10 in relation to the infrared element 3.

By distance parameter 21 it is meant the distance between the infrared element 3 and the skin trauma 10.

Such parameter, preferably determined by a distance sensor 4 (via ultrasound or laser), can be displayed in any of the screens of device 1, separately or together with the image parameters 22 or the temperature parameters 20. In reference to FIG. 3(b), a visible light beam such as a marker M, may indicate to the medical professional the exact point of the trauma 10 at which the distance parameter 21 is being generated.

FIG. 3(b) shows an illustration of the distance parameter 21 in conjunction with the image parameters 22 of the skin trauma 10.

A functionality of the proposed device 1 still related to the image parameters 22 of the skin trauma 10 lies in the possibility of having a temperature map 22''' of the trauma 10 illustrated for the medical professional.

Figure 4:
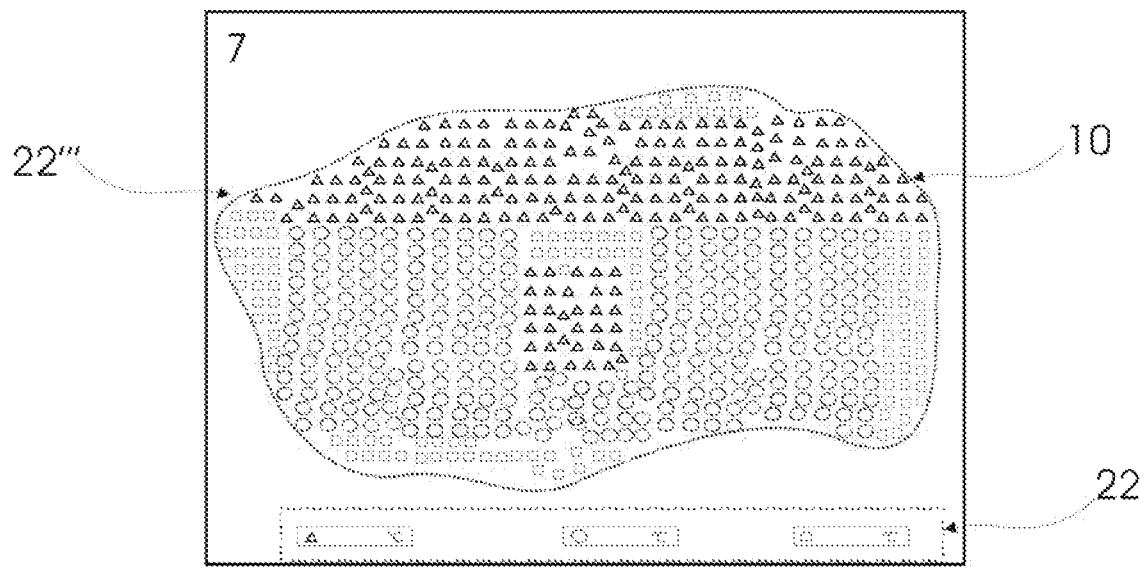
FIG. 4 is a display of the screen of the portable device proposed in the present invention illustrating a temperature map of the skin trauma.

In this regard, FIG. 4 is a display of the screen 7 of device 1 when the function selected by the doctor is that of illustrating a temperature map 22'''. For a better understanding of the map 22''', the different temperature ranges were represented by the following symbols: "Δ" (triangle), "◯" (circumference) and "□" (square).

Figure 5:
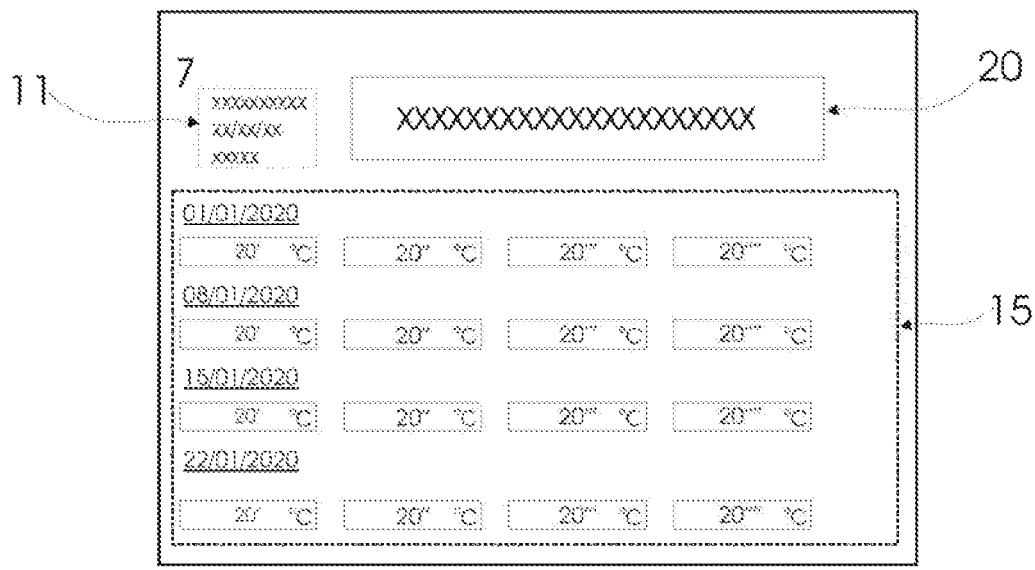
FIG. 5 is a display of the screen of the portable device proposed in the present invention illustrating a history of analysis related to the temperature parameters.

Thus, in reference to FIG. 5, each symbol must be interpreted as representing a temperature range of the skin trauma 10. For example, the display of a Δ may represent a temperature range in that region of the skin trauma 10 of 36° C. (between 36.0° C. and 36.9° C.).

In turn, the display of "◯" may represent temperature values below 35.9° C. Consequently, the display of "□" must be understood as the region where the temperature is above 37° C.

It should be noted that the inclusion of the mentioned symbols in FIG. 4 have the sole purpose of providing a better understanding of device 1 and the functionalities thereof. When in use, the temperature map 22''' can and should be illustrated by colors, thereby continuously indicating the highest (red-"□") temperature, an intermediate temperature (yellow-"Δ") and a lower value range (blue-◯). It should be noted that the display of three value ranges (temperatures) must be understood as a preferred description of the present invention. Alternatively, the temperature map 22''' could indicate an amount of ranges determined by the medical professional.

In addition, the value ranges that each symbol represents may be adapted according to the requirements of the medical professional that uses the device 1; for example, the reference temperature of 36° C. may be adjusted according to the interest of the medical professional.

Moreover, the first temperature detected for a given skin trauma 10 can be used as a reference temperature, so that the next analyses made for the same trauma 10 will display lower, higher or equal temperatures to the first temperature detected.

In addition to displaying to the medical professional each of the temperature parameters 20, distance parameters 21 and image parameters 22, the proposed device 1 may provide the doctor with the geometry 22' of the skin trauma in regions comprising a given temperature above or below a set threshold.

More specifically, and at the discretion of the medical professional, device 1 may illustrate, for example, the geometry 22' of the skin trauma 10 in regions of the trauma that are below body temperature (temperature is defined by the medical professional). Thus, device 1 is able to combine two or more of the temperature 20, distance 21 and image 22 parameters.

It should be noted that the analyses of the skin trauma 10 related to the temperature 20 parameters, distance 21 parameters and image 22 parameters as well as the analyses related to the combination of said parameters must be saved to a storage element of device 1.

The storage element can be configures as a memory card (such as a SD micro card), thus allowing the user to expand the storage capacity of device 1. A hard disk having a factory preset storage capacity may be additionally used.

The option of storing only in SD micro or hard disk is also acceptable, as well as any other storage elements known in the art.

The storage of the analyses of the skin trauma 10 provides the device 1 with one more important functionality related to the possibility of generating a history of analyses 15 of at least the one of the temperature 20, distance 21 and image 22 parameters generated at different periods of time.

For example, considering a particular patient that has suffered a skin trauma 10 such as that represented in FIG. 2 and that needs medical follow-up for a period of one month.

Throughout the analyzes performed in this period, it is up to the medical professional to choose whether to evaluate the history of analyses 15 related to only one of the temperature

20, distance 21 and image 22 parameters or whether to evaluate the history of analyses of all parameters or of the combination thereof.

FIG. 5 is a display of the screen 7 of the portable device 1 when the function selected by the medical professional is that of evaluation of the history of analyses 15 related to the temperature 20 parameters.

Only preferably, a field for patient data 11 such as name, date of birth, start date of the analysis of the healing process, location and cause of the skin trauma 10 is illustrated.

We must further consider the history of analyses 15 performed at different periods of time (dates), fictitiously beginning on Jan. 1, 2020 and ending on Jan. 22, 2020. In said history 15, the doctor has, at each date, information related to the local temperature 20', mean temperature 20", maximum temperature 20''' and minimum temperature 20''''.

Figure 6:
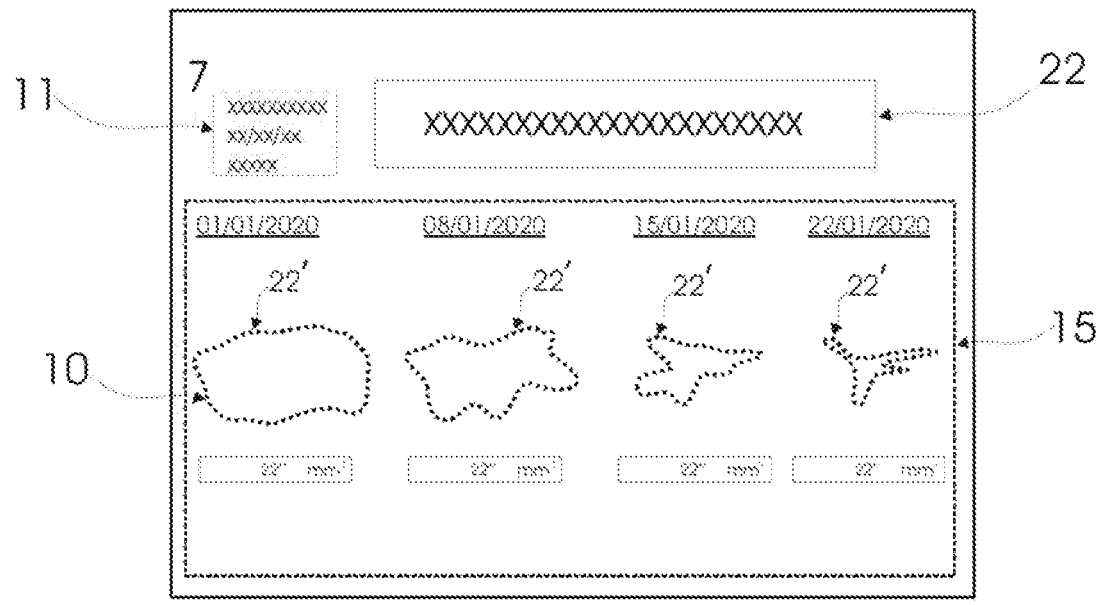
FIG. 6 is a display of the screen of the portable device proposed in the present invention illustrating a history of analysis related to the image parameters.

In addition, FIG. 6 shows a preferred embodiment of the history of analyses 15 related to the image 22 parameters, wherein the geometry 22' and the area 22" of the skin trauma 10 is highlighted at each period of time (data) of the analysis.

With such history of analyses 15, the medical professional can easily view a reduction of the geometry 22' and, consequently, a reduction in the area 22" of the skin trauma 10.

Thus, with the history of analyses 15 of the proposed device 1, it can be verified if the healing process is satisfactorily proceeding and thereby facilitating the diagnosis of the medical professional.

It should be noted that illustration of the history of analyses 15 as shown in FIGS. 5 and 6 is only a preferred arrangement and must not be considered as a limitation of the present invention.

Alternatively, the history of analyses 15 related to the image 22 parameter could further display the analyses of the temperature map 22''' and the dimensions between the outermost edges 22''''.

A screen 7 for simultaneously displaying the history 15 related both to the temperature 20 and the image 22 parameter would be also acceptable.

In other words, the form the history of analyses 15 is displayed does not represent a preferred aspect of the present invention, what is proposed is a portable device 1 for the analyses of skin traumas 10 configured and able to generate said history of analyses 15 and to provide it to the medical professional.

Based on the generated history of analyses 15, the portable device proposed in the present invention is able to generate at least one diagnosis parameter 23 related to at least one of the temperature parameters 20, distance parameters 21 and image parameters 22.

The diagnosis 23 parameter must be considered as an embodiment, in absolute or percent value, of the comparison of at least one of the temperature 20, distance 21 and image 22 parameters generated at different periods of time.

Thus, the diagnosis 23 parameter provides to the medical professional, by means of a numerical value, fast information on the healing process of the skin trauma 10.

Figure 7:
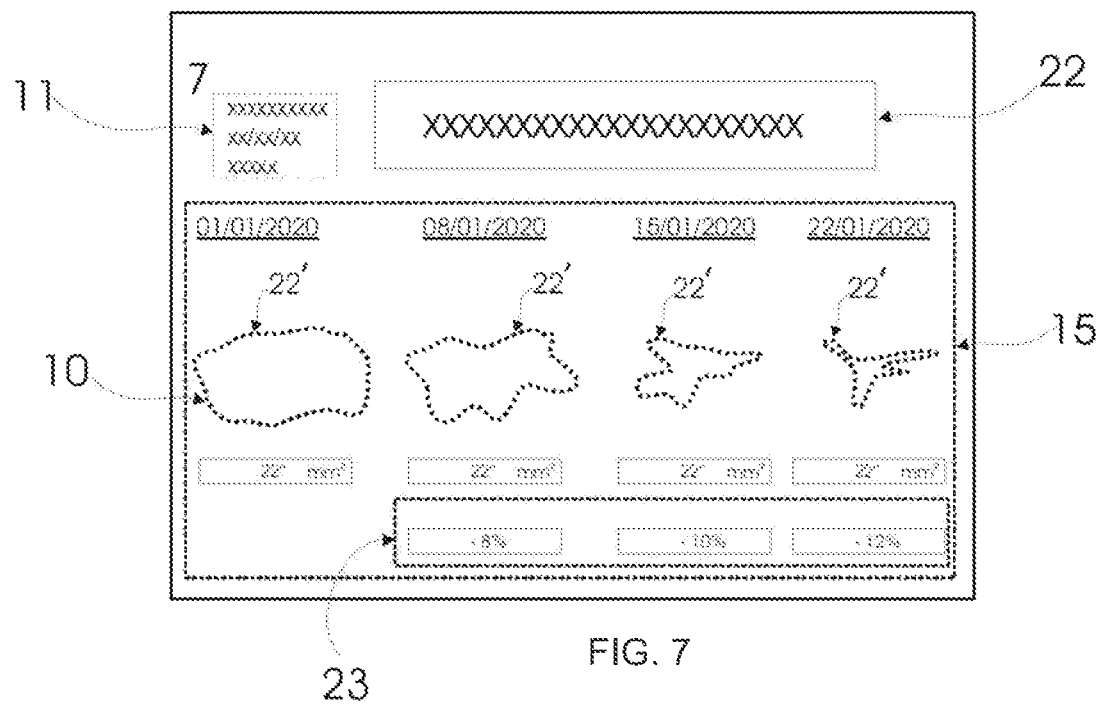
FIG. 7 is a display of the screen of the portable device proposed in the present invention illustrating a history of analysis and a diagnosis parameter related to the image parameters.

FIG. 7 is a preferred embodiment of the screen 7 of device 1 representing the illustration of the diagnosis 23 parameter related to the image 22 parameter.

In this preferred embodiment, the diagnosis 23 parameter is represented as a percentage variation of the area 22" of the skin trauma. Thus, in addition to the information provided to the doctor on the geometry 22' and area 22" of the skin trauma 10, device 1 further provides a variation of area 22" related to the analyses performed at different periods of time.

Therefore, and in reference to FIG. 7, the medical professional will know that, in Jan. 8, 2020, the area of the skin trauma 10 had a reduction of approximately 8% in relation to area 22" of the wound, when analyzed on Jan. 1, 2020. Similarly, the doctor will be informed that on Jan. 22, 2010 area 22" was reduced in 22% in relation to the analysis of Jan. 15, 2020.

It should be noted that is up to the medical professional to determine whether the diagnosis 23 parameter must be generated for the immediately preceding analysis or for the first analysis performed for a particular patient.

Furthermore, the illustration of the diagnosis 23 parameter related to area 22" must be considered only a preferred embodiment, so that the proposed device 1 is configured to generate diagnosis parameters also related to the temperature 20 and distance 21 parameters, as well as to the combination thereof.

For example, device 1 is further configured to display the diagnosis 23 parameter related to absolute or percent variations of the local temperature 20', mean temperature 20", maximum temperature 20''' and minimum temperature 20'''' of the skin trauma 10.

In terms of hardware and as already mentioned, device 1 comprises an infrared element 3, which is preferably configured as an infrared camera and is capable of generating the temperature parameters 20 discussed above.

Additionally, the device further comprises a distance sensor 4 which is able to generate a distance parameter of the skin trauma 10 in relation to the infrared element.

Associated with the infrared element 3 and the distance sensor 4, device 1 also comprises a microprocessor responsible for receiving the parameters from the infrared element 3 and distance sensor 4 and interpreting them, thereby generating the image parameters 22 as well as the history of analyzes 15 and the diagnosis parameters 23.

Thus, it can be established that the temperature 20 and distance 21 parameters are generated together both by the infrared element 3, as well as by the distance sensor 4 and microprocessor.

In addition, and based on the image of the skin trauma 10 captured by the infrared element 3, the microprocessor is configures so as to generate the image parameters 22 of the trauma 10.

More specifically, the microprocessor is configured so as to generate and display to the professional the geometry 22', the area 22", the temperature map 22''' and the dimensions between the outermost edges 22'''' of the skin trauma 10.

In parallel, both the history of analyses 15 and the diagnosis parameter 23 are also generated by the microprocessor.

As previously mentioned, the portable device 1 further comprises at least one storage element, such as an internal or also expandable memory able to store at least one of the temperature 20, distance 1 and image 22 parameters of the skin trauma 10.

Also, the portable device 1 may comprise a connection module for transmitting at least one of the temperature 20, distance 21 and image 22 parameters to a monitoring center of a hospital unity or even to a remote electronic device of the medical professional, such as a personal computer.

Said connection module may be preferably configured as a bluetooth, radiofrequency, wi-fi module or any other means of connecting and transmitting data known in the art.

In accordance with the abovementioned portable device 1, the present invention relates to a method for analyzing skin traumas using said portable device 1.

More specifically, the method for analyzing skin traumas using a portable device comprises the steps of: directing the portable device 1 to the skin trauma 10 and generating a temperature parameter 20 and a distance parameter 21 of the skin trauma 10, the temperature parameter 20 corresponding to at least one of the following skin trauma parameters 10: local temperature 20', mean temperature 20", maximum temperature 20'" and minimum temperature 20"".

Additionally, the method further comprises a step of generating a image parameter 22 of the skin trauma, the image parameter 22 being related to at least one of the following skin trauma 10 parameters: geometry 22', area 22", temperature map 10'" and dimensions between the outermost edges 22"".

The proposed method also comprises the step of generating a history of analyses 15 of at least one of the temperature 20, distance 21 and image 22 parameters generated at different periods of time and the step of: Generating at least one diagnosis parameter 23 related to the history of analyses 15, said diagnosis parameter 23 being generated from the absolute or percent comparison of at least one of the temperature 20, distance 21 and image 22 parameters generated at different periods of time.

Finally, and in accordance with the previously described portable device 1 as well as with its functionalities, the method for analyzing skin traumas further comprises the steps of: displaying, on a screen 7 of the portable device 1, at least one of the temperature 20, distance 21, image 22, diagnosis 23 parameters and history of analyses 15 of the skin trauma 10, and indicating on the screen 7 of the portable device 1 the location of at least one of the local temperature 20', maximum temperature 20'" and minimum temperature 20"" of the skin trauma 10.

Said device 1, having the aforementioned functionalities, can be used by health professionals in emergency care units, intensive care units, and as first aid kits in ambulances, fire fighting teams or by health units in major events.

In addition, the device 1 proposed in the present invention can be also used in surgical centers to rapidly detect the temperature of the patient or certain portions of its body.

Thus, the medical professional will detect abrupt temperature decrease/increase which will help in the decision making during the surgical procedure.

As an example, and without causing any limitation of its use, device 1 can be used in organ transplant surgeries or in lower limb vascular surgeries for detecting the occurrence of ischemia (which causes amputation of the limb or even death of the patient).

So, with the portable device 1 and the method for analyzing skin traumas proposed in the present invention, the medical professional has the possibility of using a portable device able to rapidly analyze the skin trauma 10 of a given patient as well as the entire healing process and history of said trauma.

Upon describing an example of preferred embodiment, it should be understood that the scope of the present invention encompasses other possible variations and is only limited by the content of the appended claims, therein included possible equivalents.

The invention claimed is:

1. A portable device for analyzing skin traumas, the portable device comprising:
   a main body;
   a plurality of navigation keys disposed on a first surface of the main body;
   a screen disposed on the first surface of the main body;
   at least one infrared camera disposed on a second surface of the main body, the at least one infrared camera being configured to generate at least one thermal image of a skin trauma;
   at least one distance sensor associated with the main body and configured to generate at least one distance parameter of the skin trauma in relation to the at least one infrared camera; and
   a microprocessor associated with the at least one infrared camera, the microprocessor being configured to generate at least one temperature parameter and at least one image parameter from the at least one thermal image, wherein the at least one image parameter is at least one of the following parameters of the skin trauma: a geometry, an area, a temperature map and dimensions between the outermost edges, the microprocessor being further configured to generate for display on the screen of the portable device a history of analysis with data collected over a plurality of different periods of time, the history of analysis comprising the geometry and the area of the skin trauma highlighted at each different period of time of the plurality of different periods of time, the portable device being small-sized and portable such that it can be transported by a medical professional in his or her pocket, the temperature map being illustrated by colors.

2. The portable device according to claim 1, wherein the at least one temperature parameter corresponds to at least one of the following parameters of the skin trauma: local temperature, mean temperature, maximum temperature, and minimum temperature.

3. The portable device according to claim 2, wherein the screen is configured to display to a user of the device the location of at least one of the local temperature, maximum temperature and minimum temperature of the skin trauma.

4. The portable device according to claim 3, wherein:
   the at least one infrared camera is configured to generate at least one thermal image of the skin trauma at each different period of time of the plurality of different periods of time;
   the at least one distance sensor is configured to generate at least one distance parameter of the skin trauma at each different period of time of the plurality of different periods of time;
   the microprocessor is configured to generate at least one temperature parameter from the at least one thermal image generated at each different period of time of the plurality of different periods of time; and
   the history of analysis further comprises the at least one distance parameter, and the at least one temperature parameter generated for each different period of time of the plurality of different periods of time.

5. The portable device according to claim 4, wherein the microprocessor is further configured to generate at least one diagnosis parameter related to the history of analysis, the at least one diagnosis parameter being generated by at least one of: a comparison of at least one temperature parameter generated at one period of time of the plurality of different periods of time with at least one temperature parameter generated at a different period of time of the plurality of different periods of time, and a comparison of at least one image parameter generated at one period of time of the plurality of different periods of time with at least one image parameter generated at a different period of time of the plurality of different periods of time.

6. The portable device according to claim 5, wherein the at least one diagnosis parameter is related to at least one of: an absolute or percent variation of the at least one temperature parameter generated at one period of time of the plurality of different periods of time and the at least one temperature parameter generated at a different period of time of the plurality of different periods of time, and an absolute or percent variation of the at least one image parameter generated at one period of time of the plurality of different periods of time and the at least one image parameter generated at a different period of time of the plurality of different periods of time.

7. The portable device according to claim 6, wherein the screen is configured to display to a user of the portable device at least one of the at least one temperature parameter, the at least one distance parameter, the at least one diagnosis parameter, and the history of analysis.

8. The portable device according to claim 7, further comprising at least one storage camera configured to store at least one of the at least one temperature parameter, the at least one distance parameter, the at least one image parameter, the history of analysis, and the at least one diagnosis parameter of the skin trauma, wherein the portable device further comprises a communication module configured to transmit at least one of the at least one temperature parameter, the at least one distance parameter, and the at least one image parameter of the skin trauma to a remote device.

9. The portable device according to claim 1, wherein the temperature map continuously indicates the highest temperature in red, an intermediate temperature in yellow, and a lower value range in blue.

10. A method for analyzing skin traumas using a portable device, the method comprising:
  directing the portable device to a skin trauma, the portable device being, small-sized and portable such that it can be transported by a medical professional in his or her pocket, the portable device comprising:
    a main body;
    a plurality of navigation keys disposed on a first surface of the main body;
    a screen disposed on the first surface of the main body;
    at least one infrared camera disposed on a second surface of the main body, the at least one infrared camera being configured to generate at least one thermal image of a skin trauma;
    at least one distance sensor associated with the main body and configured to generate at least one distance parameter of the skin trauma in relation to the at least one infrared camera; and
    a microprocessor associated with the at least one infrared camera,
      the microprocessor being configured to generate at least one temperature parameter and at least one image parameter from the at least one thermal image,
      the microprocessor being further configured to generate for display on the screen of the portable device a history of analysis with data collected over a plurality of different periods of time,
      the history of analysis comprising a geometry and an area of the skin trauma highlighted at each different period of time of the plurality of different periods of time;
  generating the at least one thermal image and the at least one distance parameter of the skin trauma, and generating the at least one temperature parameter and the at least one image parameter of the skin trauma from the at least one thermal image wherein
    the at least one temperature parameter corresponding to at least one of the following skin trauma parameters: local temperature, mean temperature, maximum temperature, and minimum temperature, and
    the at least one image parameter corresponding to at least one of the following skin trauma parameters: the geometry, the area, a temperature map illustrated by colors, and dimensions between the outermost edges; and
  generating, with the microprocessor, for display on the screen of the portable device the history of analysis with data collected over the plurality of different periods of time, the history of analysis comprising the geometry, the area, or a temperature of the skin trauma highlighted at each different period of time of the plurality of different periods of time.

11. The method according to claim 10, further comprising:
  generating the at least one thermal image of the skin trauma at each different period of time of a plurality of different periods of time;
  generating at least one temperature parameter from the at least one thermal image generated at each different period of time of the plurality of different periods of time;
  generating at least one distance parameter of the skin trauma at each different period of time of a plurality of different periods of time;
  generating the history of analysis comprising the at least one distance parameter, and the at least one temperature parameter generated for each different period of time of the plurality of different periods of time; and
  generating at least one diagnosis parameter related to the history of analysis, the at least one diagnosis parameter being generated by an absolute or percent comparison of at least one temperature parameter generated at one period of time of the plurality of different periods of time with at least one temperature parameter generated at a different period of time of the plurality of different periods of time, and a comparison of at least one image parameter generated at one period of time of the plurality of different periods of time with at least one image parameter generated at a different period of time of the plurality of different periods of time.

12. The method according to claim 11, further comprising:
  displaying, on the screen of the portable device, at least one of the at least one temperature parameter, the at least one distance parameter, and the at least one diagnosis parameter; and
  indicating, on the screen of the portable device, the location of at least one of the local temperature, maximum temperature, and minimum temperature of the skin trauma.

13. The method according to claim 12, further comprising:
  storing at least one of the at least one temperature parameter, the at least one distance parameter, the at least one image parameter, the history of analysis, and the at least one diagnosis parameter of the skin trauma; and
  sending at least one of the at least one temperature parameter, the at least one distance parameter, the at least one image parameter, the history of analysis, and the at least one diagnosis parameter of the skin trauma to an electronic device remote from the portable device.

14. The method according to claim 10, wherein the temperature map continuously indicates the highest temperature in red, an intermediate temperature in yellow, and a lower value range in blue.

* * * * *